US012569298B2

(12) United States Patent　　　(10) Patent No.:　US 12,569,298 B2
Brinkmann et al.　　　　　　　　(45) Date of Patent:　Mar. 10, 2026

(54) DISTANCE MEASURING METHOD AND DEVICE AS WELL AS LASER LITHOTRIPSY DEVICE

(71) Applicant: KARL STORZ SE & Co. KG, Tuttlingen (DE)

(72) Inventors: Ralf Brinkmann, Luebeck (DE); Birgit Lange, Luebeck (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 975 days.

(21) Appl. No.: 17/740,747

(22) Filed: May 10, 2022

(65) Prior Publication Data

US 2022/0361951 A1　　Nov. 17, 2022

(30) Foreign Application Priority Data

May 12, 2021　(DE) ..................... 10 2021 112 411.5

(51) Int. Cl.
　*A61B 18/26*　　(2006.01)
　*A61B 18/00*　　(2006.01)
　*G01S 17/08*　　(2006.01)
(52) U.S. Cl.
　CPC .............. *A61B 18/26* (2013.01); *G01S 17/08* (2013.01); *A61B 2018/00702* (2013.01)
(58) Field of Classification Search
　CPC .......... A61B 18/26; A61B 2018/00702; A61B 2017/00066; A61B 2018/00642;
(Continued)

(56) References Cited

U.S. PATENT DOCUMENTS

2008/0093540 A1　　4/2008　Horimoto et al.
2010/0137847 A1*　6/2010　Cecchetti ............... A61B 18/26
　　　　　　　　　　　　　　　　　　　　　　　606/2.5
(Continued)

FOREIGN PATENT DOCUMENTS

DE　　　　19546873 C1　　5/1997
DE　　102014226827 A1　　6/2016
(Continued)

OTHER PUBLICATIONS

European Search Report for European Patent Application No. 22171604.6, mailed Oct. 10, 2022.
(Continued)

*Primary Examiner* — Seung C Sohn
(74) *Attorney, Agent, or Firm* — Jason H. Vick; Amped IP LLC

(57)　　　　　　ABSTRACT

A measuring method for optically determining a distance (z) of a surface located in a medium from an end of an optical waveguide is described and has the following steps: emitting electromagnetic measuring radiation of a first wavelength ($\lambda1$) and of a second wavelength ($\lambda2$) from the end of the waveguide towards the surface, wherein the medium more strongly absorbs the electromagnetic measuring radiation of the second wavelength ($\lambda2$) than the electromagnetic measuring radiation of the first wavelength ($\lambda1$); measuring a first reflection signal ($I_1$) of the electromagnetic measuring radiation of the first wavelength ($\lambda1$) reflected from the surface, and measuring a second reflection signal ($I_2$) of the electromagnetic measuring radiation of the second wavelength ($\lambda2$) reflected from the surface, and determining the distance (z) from a ratio ($I_2$:$I_1$) of the second and the first reflection signal. Furthermore, a measuring device and a laser lithotripsy device are described.

17 Claims, 6 Drawing Sheets

(58) Field of Classification Search
CPC   A61B 2018/00672; A61B 2018/00678; A61B
2018/00785; A61B 2090/061; G01S
17/08; G01B 11/026
See application file for complete search history.

(56)                    References Cited

U.S. PATENT DOCUMENTS

| | | | |
|---|---|---|---|
| 2013/0123769 A1 | 5/2013 | Khatchaturov et al. | |
| 2015/0289937 A1* | 10/2015 | Chia .................. | A61B 1/00009 |
| | | | 606/2.5 |
| 2016/0135894 A1* | 5/2016 | Finkman ................ | A61B 1/307 |
| | | | 606/15 |
| 2016/0178508 A1 | 6/2016 | Ramsteinder | |
| 2021/0378745 A1 | 12/2021 | Fukushima et al. | |
| 2023/0350021 A1 | 11/2023 | Khachaturov et al. | |

FOREIGN PATENT DOCUMENTS

| | | | |
|---|---|---|---|
| DE | 202016103544 U1 | 7/2017 | |
| EP | 3725213 A1 | 10/2020 | |
| FR | 2739445 A1 | 4/1997 | |
| WO | WO 84/04439 A1 | 11/1984 | |
| WO | WO 2020/174686 A1 | 9/2020 | |
| WO | WO 2021/026161 A1 | 2/2021 | |
| WO | WO 2021/144801 A1 | 7/2021 | |
| WO | WO 2022/112977 A1 | 6/2022 | |

OTHER PUBLICATIONS

Komives, Clair et al. "Fiber-Optic Fluorometer Signal Enhancement and Application to Biosensor Design" Talanta 1992, 39(4): 429-441, Abstract Only.
Lange, Birgit et al. "Exploiting the Aiming Beam to Increase the Safety of Laser Lithotripsy: Experimental Evaluation of Light Reflection and Fluorescence" Lasers Surg Med.; 2020; 52(5); 456-471; Abstract Only.
Lange, Birgit et al. "Stone/Tissue Differentiation for Holmium Laser Lithotripsy Using Autofluorescence" Lasers Surg Med; 47(9): 737-744; Sep. 22, 2015; Abstract Only.
Schlager, Daniel et al. "A Novel Laser Lithotripsy System with Automatic Real-Time Urinary Stone Recognition: Computer Controlled Ex Vivo Lithotripsy is Feasible and Reproducible in Endoscopic Stone Fragmentation" The Journal of Urology; vol. 202; Issue 6; Dec. 2019; pp. 163-1269; Abstract Only.
Svyryd, V. et al. "An Analysis of a Displacement Sensor Based on Optical Fibers" Revista Meixana de Fisica S 52(2): 61-63 (2006).
Office Action for corresponding German Patent Application No. 102021112411.5, mailed Feb. 10, 2022.
Office Action for corresponding German Patent Application No. 102021112411.5, mailed Feb. 27, 2025.
Office Action for corresponding European Patent Application No. 22171604.6, mailed Apr. 25, 2025.

* cited by examiner

Fig. 3a
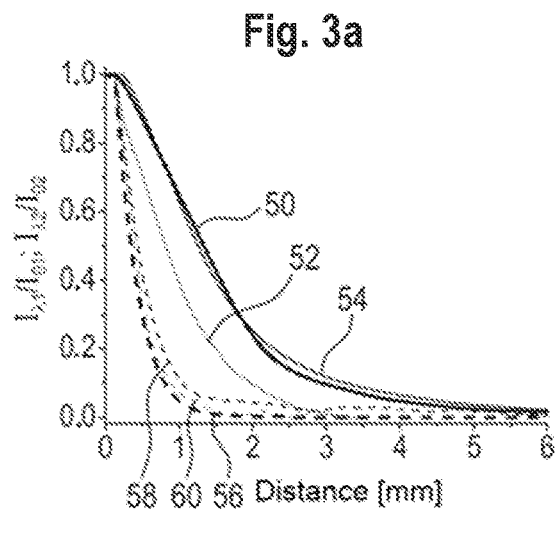
Fig. 3b
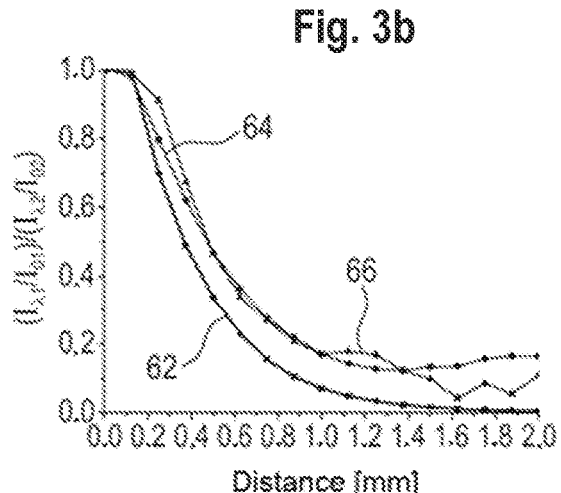
Fig. 4a
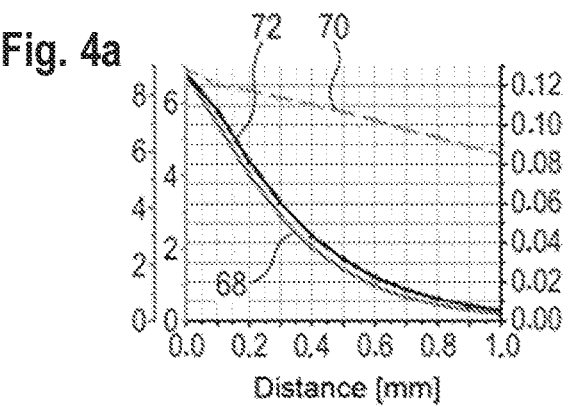
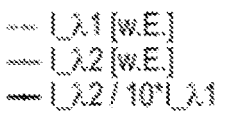
Fig. 4b
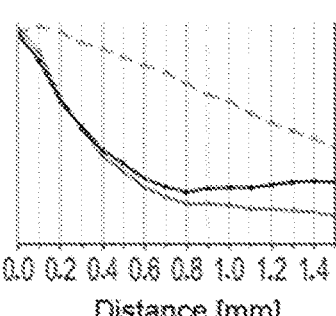
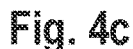
Fig. 4c
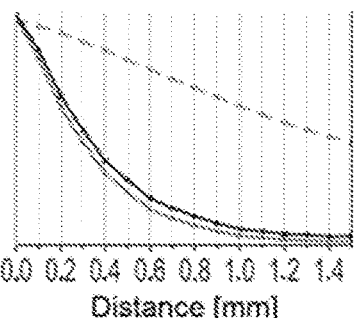
Fig. 4d
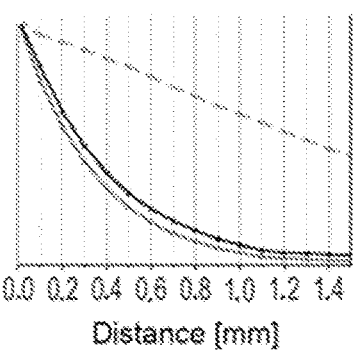
Fig. 4e
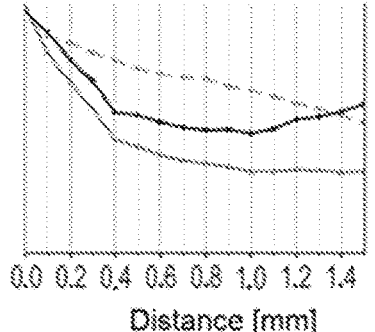

DISTANCE MEASURING METHOD AND DEVICE AS WELL AS LASER LITHOTRIPSY DEVICE

CROSS-REFERENCE TO RELATED APPLICATIONS

This application claims the benefit under 35 U.S.C. 119(a) to German Patent Application No. 10 2021 112 411.5, filed 12 May 2021, the disclosure of which is incorporated herein by reference in its entirety.

BACKGROUND

An exemplary embodiment of the invention relates to a measuring method for optically determining a distance of a surface of a body stone located in a medium from an end of an optical waveguide.

The disclosed technology also relates to a measuring device for optically determining a distance of a surface of a body stone located in a medium from an end of an optical waveguide.

Lastly, the disclosed technology relates to a laser lithotripsy device for breaking up body stones.

Laser lithotripsy is an established way of treating body stones, for example stones in the bladder or in the ureter. In the case of laser lithotripsy, in order to break up stones, laser light is directed via an optical waveguide, for example an optical fiber, at the stone to be broken up. In order to break up the stones, different techniques are used which differ in pulse repetition rate and pulse energy of the laser beam and positioning and movement of the optical waveguide. The breaking-up process is essentially most effective when the end of the optical waveguide, from which the laser light exits, is in contact with or very close to the stone.

Virtually all human body stones emit an autofluorescence signal when excited with green light. This autofluorescence signal can be used during the laser lithotripsy for automatic stone detection, as described for example in the article by Lange B., Cordes J., Brinkmann R.: "Stone/tissue differentiation for holmium laser lithotripsy using autofluorescence"; Lasers Surg Med 2015; 47(9): 737-744. In the case of existing technical implementations of an automatically controlled Holmium laser system, the laser is only triggered when the fluorescence signal has exceeded a previously specified threshold value (see Schlager D., Miernik A., Lamrini S. et al.: "A novel laser lithotripsy system with automatic real-time urinary stone recognition: Computer controlled ex vivo lithotripsy is feasible and reproducible in endoscopic stone fragmentation"; Journal of Urology 2019; 202: 1263-1269). In this case however, the problem has been found that the intensity of the fluorescence of different stones is different in strength, whereby the distance between the end of the optical waveguide and the stone can disadvantageously vary by multiple millimeters when this threshold value is exceeded.

It has already been proposed to integrate a reflection measurement in the development of stone detection by means of fluorescence measurement, as described in the article by Lange B., Cordes J., Brinkmann R.: "Exploiting the aiming beam to increase the safety of laser lithotripsy: Experimental evaluation of light reflection and fluorescence"; Lasers Surg Med 2020; 52(5); 456-471. If there is no surface located in front of the exit end of the treatment fiber, conclusions can be drawn from the reflection signal about the state of the fiber end surface. Surfaces in front of the fiber lead to a distance-dependent signal increase. However, this disadvantageously varies with the surface structure and the reflectance of the surface of the respective stone such that a sufficiently accurate distance measurement is not made possible.

When the end of the optical waveguide, with which the treatment laser light is supplied, is spaced too far apart from the stone to be broken up, not only is the effect of the treatment laser light in relation to the breaking up of the stone reduced to an undesired extent, which can lead to a significant temperature rise in the treatment volume in the case of insufficient purge flow, but rather there is also the danger that the treatment laser light impacts uninvolved tissue and damages it.

The distance of the exit end of the waveguide, via which the treatment laser light is emitted, is therefore an important operating parameter of the laser lithotripsy device.

One object underlying the invention is to provide a measuring method and a measuring device, with which this operating parameter can be determined with greater accuracy.

Another object also underlying the invention is to provide an improved laser lithotripsy device.

According to the invention, a measuring method is provided for optically determining a distance of a surface of a body stone located in a medium from an end of an optical waveguide, having the steps:

emitting electromagnetic measuring radiation of a first wavelength and of a second wavelength from the end of the waveguide towards the surface, wherein the medium more strongly absorbs the electromagnetic measuring radiation of the second wavelength than the electromagnetic measuring radiation of the first wavelength;

measuring a first reflection signal of the electromagnetic measuring radiation of the first wavelength reflected from the surface, and measuring a second reflection signal of the electromagnetic measuring radiation of the second wavelength reflected from the surface, and determining the distance from a ratio of the second and the first reflection signal.

According to the invention, a measuring device is provided for optically determining a distance of a surface of a body stone located in a medium from an end of an optical waveguide, having:

a measuring radiation source for generating electromagnetic measuring radiation of a first wavelength and of a second wavelength, wherein the medium more strongly absorbs the electromagnetic measuring radiation of the second wavelength than the electromagnetic measuring radiation of the first wavelength, an optical waveguide for emitting the electromagnetic measuring radiation from the end of the waveguide towards the surface;

a detection device for measuring a first reflection signal of the electromagnetic measuring radiation of the first wavelength reflected from the surface, and for measuring a second reflection signal of the electromagnetic measuring radiation of the second wavelength reflected from the surface, and an evaluation unit for determining the distance from a ratio of the second and the first reflection signal.

Using the measuring method according to the invention and the measuring device according to the invention, the distance of an end of an optical waveguide from the surface of a target object can be reliably determined. The waveguide can in particular be an optical fiber, in particular a multi-mode fiber. According to the invention, electromagnetic measuring radiation with at least two different wavelengths is directed from the end of the waveguide at the surface of the object. The first and the second wavelength are selected such that the measuring radiation of the one wavelength is more strongly absorbed by the medium than the measuring radiation of the other wavelength. The measured reflection signals therefore present a different dependency on the distance of the end of the optical waveguide from the surface of the target object on which the measuring radiation is reflected. In other words, the reflection signal of the measuring radiation of the wavelength that is more strongly absorbed, decreases more quickly as a function of the distance than the reflection signal of the other wavelength.

The term "reflection" includes in the context of the present invention not only directed, i.e. mirroring reflection, but also diffuse, i.e. scattered reflection. By using measuring radiation of at least two wavelengths with different absorption and the ratio calculation from the associated reflection signals, different reflectances of different surfaces do not or, to a notably reduced extent, negatively impact the measurement result of the distance measurement, in particular when the reflectances are not or only slightly wavelength-dependent, but at least notably less dependent on the wavelength than the absorption in the medium. In contrast, when the distance measurement is carried out with only one wavelength, it is not possible to make conclusions from the intensity of the reflection signal about the distance between the surface and the end of the optical waveguide since the reflection ability of surfaces of different bodies can vary significantly and this also applies to body stones.

The medium can in particular be a fluid medium, for example water or an aqueous solution or also a gaseous medium, which absorbs to different extents in the case of different wavelengths.

The measuring method according to the invention or the measuring device according to the invention can in particular be used for determining the operating parameter 'Distance of an end of a treatment fiber from the surface of a stone' in a laser lithotripsy device. However, it is understood that the measuring method according to the invention is not limited to an application in laser lithotripsy, but rather can be used generally in measuring technology for distance measurement.

The measuring method according to the invention is suitable in particular for determining small distances in the range of a few tenths of millimeters up to a few millimeters.

The first wavelength can be selected such that it is not absorbed or only slightly absorbed by the medium, while the second wavelength is preferably selected such that, due to the stronger absorption, the second reflection signal decreases within a desired distance range to less than a fraction of the maximally measurable intensity.

In a preferred embodiment, the determination of the distance can include determining whether a predetermined maximum distance is undercut. For some applications, for example in laser lithotripsy, it is not necessary to know the exact value of the measured distance, but only whether the measured distance is below a limit value. The evaluation of the reflection signals can be hereby simplified. Alternatively or cumulatively to the above measure, in a preferred embodiment, the determination of the distance includes determining whether a predetermined minimum distance is exceeded. This can advantageously serve to prevent the end of the waveguide coming into contact with the surface. The end or the end surface of the waveguide can therefore be protected.

The evaluation unit can generate a trigger signal when the measurement indicates that the predetermined maximum distance is undercut and/or the predetermined minimum distance is exceeded or when the measurement indicates that the measured distance is between the minimum distance and the maximum distance. Such a trigger signal can trigger an activation of a device or enable a device for the activation of the same. For example, in the context of laser lithotripsy, the trigger signal can enable the treatment laser in order to be able to then activate it.

The second wavelength is preferably selected such that the second reflection signal at a distance from the end of the waveguide below the predetermined maximum distance decreases to a fraction of less than 20%, preferably of less than 10%, further preferably of less than 5%, of the maximally measurable intensity.

In other words, the second wavelength can be selected such that only distances are detected that are shorter than a predetermined distance limit value, while in the case of distances that are greater than the distance limit value, the second reflection signal can be so weak that it does not differ from a noise. If a second reflection signal is not measured, therefore this means that the distance of the end of the waveguide from the surface of the target object is outside of the desired distance range.

In a further preferred configuration, a first threshold value can be predetermined for the second reflection signal as a function of the predetermined maximum distance and the ratio of the second reflection signal and the first reflection signal can be multiplied by 1 when the second reflection signal exceeds the threshold value for the second reflection signal, and can otherwise be set to zero, wherein, as a function of the predetermined maximum distance, a second threshold value can be predetermined for the ratio of the second reflection signal and the first reflection signal.

This measure is advantageous for a practical implementation of the measuring method and the measuring device according to the invention, when, as for example in the case of laser lithotripsy, only distances below a maximum distance are of interest. With this measure, additionally with a simple computer operation, namely the multiplication of the ratio of the reflection signals with a step function which has values 0 and 1, a simple evaluation of the reflection signals is made possible, with which distances can be reliably detected below a desired maximum distance.

In a further preferred embodiment, the second wavelength can be selected such that the absorption coefficient of the medium in the case of the second wavelength differs from the absorption coefficient in the case of the first wavelength by a factor of at least 100, preferably of at least 1000, further preferably of at least 10000.

The stronger the absorption of the measuring radiation of the second wavelength by the medium, the quicker the second reflection signal decreases with increasing distance from the end of the waveguide. A strong decrease of the second reflection signal is in particular advantageous in the case of the measurement of very small distances of less than 1 mm.

In further preferred embodiments, the first wavelength can be in the visible spectral range and/or the second wavelength in the near infrared spectral range.

The first wavelength can for example be selected such that it excites the target object to autofluoresce, as has already been used in the conventional techniques for body stone detection. The first wavelength can therefore be used to differentiate between stones and tissue. The first wavelength can for example be in the green spectral range. When the second wavelength is in the near-infrared spectral range, the measuring radiation of the second wavelength is absorbed very strongly. For example in the case of a wavelength of 1310 nm, the reflection signal of a mirror in water, depending on the numerical aperture of the waveguide and the angle of incidence on the mirror, can decrease within 1 mm to roughly 4% of the maximum value of the signal at the end of the waveguide.

According to a further aspect of the invention, alternatively or additionally to the selection of the second wavelength in such manner that the absorption coefficient of the medium in the case of this wavelength is higher than in the case of the first wavelength, in a preferred embodiment, the measuring radiation of the first wavelength can be coupled into the waveguide at a first opening angle, which differs from an opening angle, at which the measuring radiation of the second wavelength is coupled into the waveguide.

Furthermore, as part of a further aspect of the invention, the measuring radiation of the first or of the second wavelength can be coupled into the waveguide obliquely to the waveguide longitudinal axis.

Using the two measures mentioned above, which can also be used in combination with one another, it can also be achieved that one of the reflection signals decreases more quickly as a function of the distance from the end of the waveguide than the other reflection signal by the measuring radiations being coupled differently into the waveguide. In other words, by using the numerical apertures of the waveguide in different manners and/or by coupling in the measuring radiation in a 'skewed manner', the distance behavior of the reflection signals can be influenced. The different couplings of the measuring radiations provide different radiation profiles at the output of the waveguide, which lead to different distance behaviors of the reflection signals following reflection on the surface of the target object. A donut-shaped radiation profile can be generated for example on the output side of the waveguide with a skewed coupling. These measures may in particular be advantageous when, for example, a measuring radiation source is not available which can provide the measuring radiation of a wavelength which is absorbed by the medium to the desired extent. Thus, as part of this aspect, the first wavelength and the second wavelength can even be the same.

Therefore, the invention also comprises the following aspects, independently of claim 1:

measuring method for optically determining a distance of a surface located in a medium from an end of an optical waveguide, having the steps:

emitting a first electromagnetic measuring radiation and a second electromagnetic measuring radiation from the end of the waveguide towards the surface, wherein the first measuring radiation is coupled into the waveguide at a first opening angle, which differs from an opening angle at which the second measuring radiation is coupled into the waveguide, and/or the first measuring radiation or the second measuring radiation is coupled into the waveguide obliquely to the waveguide longitudinal axis;

measuring a first reflection signal of the first electromagnetic measuring radiation reflected from the surface, and measuring a second reflection signal of the second electromagnetic measuring radiation reflected from the surface, and determining the distance from a ratio of the second and the first reflection signal.

The optical waveguide can in particular be an optical fiber, in particular a multi-mode fiber.

The measuring radiation source can be a broadband measuring radiation source. The first wavelength and the second wavelength can be passed through filters arranged after the measuring radiation source, while other spectral ranges of the generated electromagnetic measuring radiation are blocked.

The measuring radiation source can, however, also have separate light sources in each case for the first wavelength, the second wavelength and, if necessary, further wavelengths, in particular a first laser for generating the electromagnetic measuring radiation of the first wavelength and a second laser for generating the electromagnetic measuring radiation of the second wavelength, as is provided in a preferred embodiment.

The detection device can have a detector, which is suitable for measuring the reflection signals of the first and of the second wavelength, wherein corresponding spectral filters can be arranged in front of the detector. A separation of the two wavelengths at the detector can also be achieved by time multiplexing. Similarly, it is possible that the detection device has a separate detector for each wavelength.

The measuring radiation source can be designed to generate the first wavelength in the visible spectral range and/or the second wavelength in the near infrared range.

As already described above, the coupling of the measuring radiation into the optical waveguide can take place such that the numerical aperture of the optical waveguide is utilized in different manners, i.e. the measuring radiation is coupled into the waveguide at different opening angles. This can be implemented by optics having different numerical apertures arranged after the light sources. Alternatively or cumulatively, as already mentioned above, the first or second measuring radiation generated by the measuring radiation source can be coupled into the waveguide obliquely to the waveguide longitudinal axis, which can be implemented by optics or by an oblique arrangement of the entry end of the waveguide relative to the direction of emission of the measuring light source.

The optical waveguide preferably has a numerical aperture of greater than 0.1, preferably greater than 0.2.

The evaluation unit can be implemented as a microprocessor which can be integrated in the detection device. The evaluation unit can, however, also be implemented as software.

Furthermore, according to the invention, a laser lithotripsy device is provided for breaking up body stones, using a treatment laser for emitting treatment laser light and a measuring device according to one or a plurality of the above-mentioned configurations.

The treatment laser light is preferably fed into the same waveguide and emitted from it, with the distance measurement also being carried out therewith.

The treatment laser can for example be a Holmium laser. In the case of lithotripsy, the medium is urine or irrigation fluid.

The evaluation unit of the measuring device can be designed to generate a trigger signal for enabling the treatment laser when a distance of the end of the waveguide is measured from the surface of a body stone to be broken up that is shorter than a predetermined maximum distance. The treatment laser is therefore only enabled for activation when the end of the waveguide is located close enough to the body stone. Additionally, the trigger signal is preferably only generated when the measured distance of the end of the waveguide from the surface of the body stone is greater than a minimum distance. In a further preferred configuration, the laser lithotripsy device can have a control device for the treatment laser designed to adjust the pulse energy of the treatment laser light as a function of the measured distance. For example, the control device can increase the pulse energy when the end of the waveguide is located at a greater distance from the surface of the body stone, or reduces it in the case of a shorter distance. The efficiency of the treatment can be hereby improved.

Further advantages and features emerge from the following description and the enclosed drawing.

It is understood that the features mentioned above and still to be explained below can be used not only in the respectively indicated combination, but also in other combinations or alone without departing from the scope of the invention.

BRIEF DESCRIPTION OF THE DRAWINGS

Exemplary embodiments of the invention are represented in the drawing and are described in more detail with reference to them hereafter, in which:

FIG. 3a) is a diagram showing reflection signals of surfaces of different target objects as a function of the distance of the respective surface from the end of an optical waveguide for two different wavelengths in each case;

FIG. 3b) is a diagram showing the respective ratio of the reflection signals for the two different wavelengths from FIG. 3a);

FIG. 4a)-e) are further diagrams showing the distance dependency of reflection signals on surfaces of different target objects for two different wavelengths as well as the ratio of the reflection signals for the two different wavelengths;

FIG. 8a)-e) are different radiation profiles of measuring radiation exiting an optical waveguide, which have been generated by different couplings of the measuring radiation into the waveguide;

DETAILED DESCRIPTION

Figure 1:
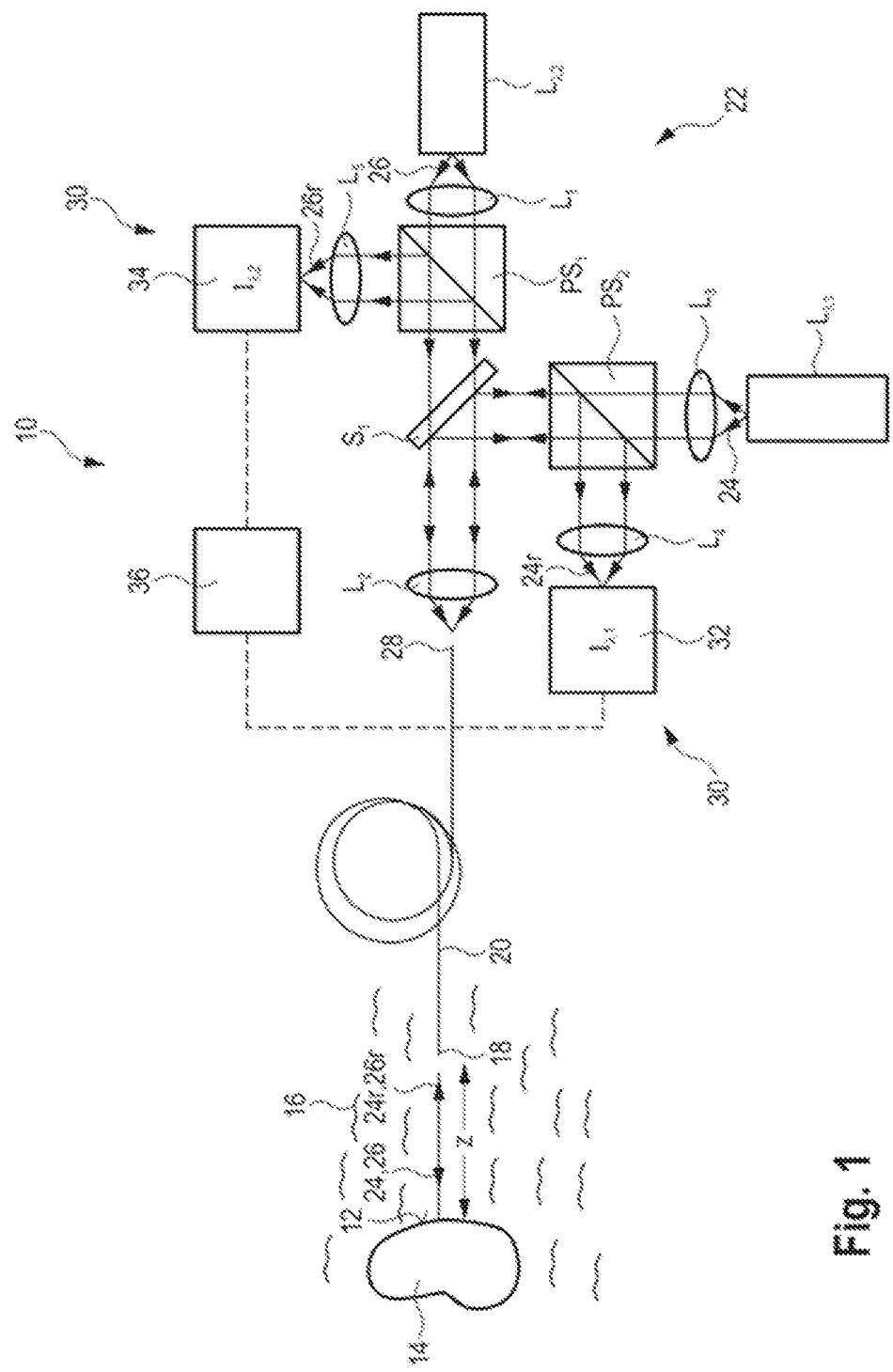
FIG. 1 is a block diagram of a measuring device for optically determining a distance of a surface located in a medium from an end of an optical waveguide.

FIG. 1 shows an exemplary embodiment of a measuring device 10 for optically determining a distance z of a surface 12 of a target object 14, which is located in a medium 16, from an end 18 of an optical waveguide 20. The medium 16 is in particular a fluid medium, for example water or an aqueous solution. The medium 16 can for example be a bodily fluid, in particular urine.

The optical waveguide 20 can for example be an optical fiber, in particular a multi-mode fiber. The optical waveguide 20 can also be a fiber bundle.

The measuring device 10 has a measuring radiation source 22 for generating electromagnetic measuring radiation of a first wavelength and of a second wavelength. In the exemplary embodiment shown, the measuring radiation source has a first laser $L_{\lambda 1}$ for generating electromagnetic measuring radiation 24 of a wavelength $\lambda 1$ and a second laser $L_{\lambda 2}$ for generating electromagnetic measuring radiation 26 of a wavelength $\lambda 2$, wherein the wavelengths $\lambda 1$ and $\lambda 2$ are different in such manner that the measuring radiation of the wavelength $\lambda 2$ is more strongly absorbed by the medium 16 than the measuring radiation of the wavelength $\lambda 1$. In other embodiments, the measuring radiation 24 and the measuring radiation 26 can also be generated together by a single light source, for example a broadband light source, which is arranged after one or a plurality of spectral filters which has or have a transmission range for the wavelengths $\lambda 1$ and $\lambda 2$.

The measuring radiation 24 and the measuring radiation 26 are, simultaneously or slightly offset in time, coupled into an entry end 28 of the optical waveguide 20 and exit the end 18, which is the exit end for the measuring light, of the waveguide.

The measuring device 10 can have a plurality of optical elements, as shown. The measuring radiation 26, which is generated by the laser $L_{\lambda 2}$, can for example be collimated by a lens $L_1$, then passes through a beam splitter $PS_1$, which can be a polarization beam splitter, and a dichroic mirror $S_1$ and is bundled by a further lens $L_2$ to an end 28 of the optical waveguide 20 opposite the end 18 and coupled into said optical waveguide. The measuring radiation 24, which is generated by the laser $L_{\lambda 1}$, is collimated by a lens $L_3$, passes through a beam splitter $PS_2$, which can be a polarization beam splitter, is deflected by the dichroic mirror $S_1$ to the lens $L_2$ and is also bundled by said lens to the end 28 of the optical waveguide 20 and coupled into said optical waveguide.

The measuring device 10 also has a detection device 30 for measuring a first reflection signal of the electromagnetic measuring radiation 24r of the first wavelength $\lambda 1$ reflected from the surface 12 and for measuring a second reflection signal of the electromagnetic measuring radiation 26r of the second wavelength $\lambda 2$ reflected from the surface 12. The reflected measuring radiation 24r of the first wavelength $\lambda 1$ enters the end 18 of the optical waveguide 20 and exits the end 28, is collimated by the lens $L_2$, deflected by the dichroic mirror $S_1$ to the beam splitter $PS_2$ and deflected thereby to a further lens $L_4$, which bundles the reflected measuring radiation 24r to a first detector 32 in order to measure a first reflection signal $I_{\lambda 1}$. The reflected measuring radiation 26r of the second wavelength $\lambda 2$ is also captured by the end 18 of the optical waveguide 20, exits the end 28, passes through the lens $L_2$ and the dichroic mirror $S_1$, is deflected by the beam splitter $PS_1$ to a further lens $L_5$ and is bundled thereby to a detector 34 in order to measure a second reflection signal Ike. In other embodiments, the detection device 30 can also have only one single detector which receives both reflected measuring radiations 24r and 26r and is sensitive to both wavelengths $\lambda 1$ and $\lambda 2$.

The measuring device 10 also has an evaluation unit 36, which evaluates the reflection signals $I_{\lambda 1}$ and $I_{\lambda 2}$ in order to determine the distance z from a ratio of the two reflection signals $I_{\lambda 1}$ and $I_{\lambda 2}$, as will be described in more detail later.

The evaluation unit 36 can also be integrated into the detection device 30 and can be implemented as a microprocessor or as software.

Figure 2:
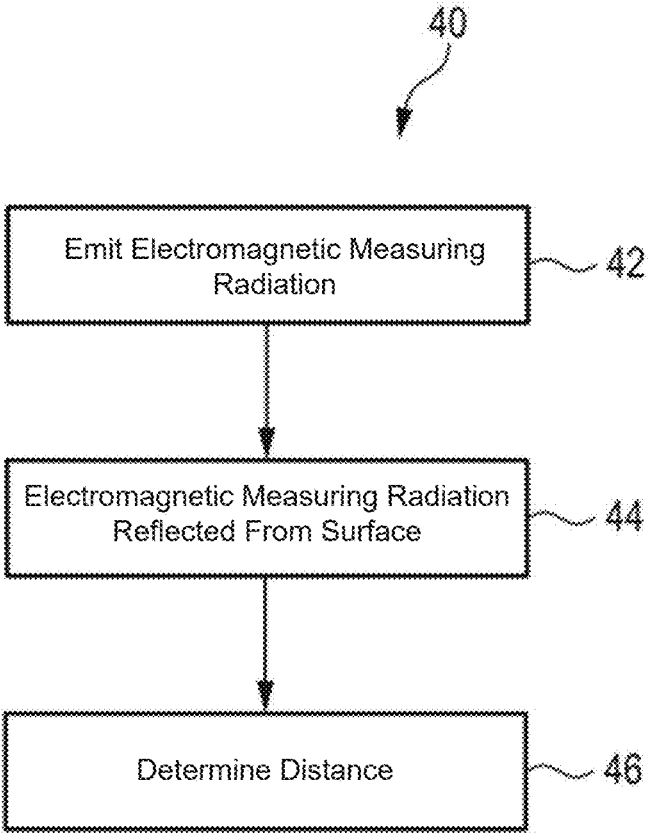
FIG. 2 is a flow diagram of a measuring method for optically determining a distance of a surface located in a medium from an end of an optical waveguide.

FIG. 2 shows a flow diagram of a measuring method 40 for optically determining a distance z of a surface 12 of a target object 14 located in a medium 16 from an end 18 of an optical waveguide 20. The measuring method 40 can be carried out using the measuring device 10 in FIG. 1, but without it being limited thereto.

In a step 42, electromagnetic measuring radiation of a first wavelength λ1 and of a second wavelength λ2 is emitted from the end 18 of the waveguide 20 towards the surface 12, wherein the medium 16 more strongly absorbs the electromagnetic measuring radiation of the second wavelength λ2 than the electromagnetic measuring radiation of the first wavelength λ1. In a step 44, a first reflection signal $I_{\lambda 1}$ of the electromagnetic measuring radiation of the first wavelength λ1 reflected from the surface 12 and a second reflection signal $I_{\lambda 2}$ of the electromagnetic measuring radiation of the second wavelength λ2 reflected from the surface 12 are measured. In a step 46, the distance of the surface 12 from the end 18 of the optical waveguide 20 is determined from a ratio of the second reflection signal $I_{\lambda 2}$ to the first reflection signal $I_{\lambda 1}$.

The wavelength λ1 is preferably selected such that the absorption of the medium 16 in the case of this wavelength λ1 is only weak. The intensity of the reflection signal $I_{\lambda 1}$ in the case of the wavelength λ1 can be described as follows:

$$I_{\lambda 1}=I_{01} \cdot r_1 \cdot d_{\lambda 1}(z) \tag{1}$$

In equation (1), $I_{01}$ is the reflection signal measured upon contact between the end 18 of the optical waveguide 20 and a highly-reflective surface (for example of a mirror) (that is to say, the maximum measurable intensity or the maximum measurable reflection signal), $r_1$ is the reflectance of the surface 12 and $d_{\lambda 1}$ (z) a function, which describes the decrease of the reflection signal with increasing distance z due to the illumination and detection geometry and depends on the numerical aperture (as described for example in the article by Komives C, Schultz J. S.: "Fiber-Optic Fluorometer Signal Enhancement and Application to Biosensor Design", Talanta 1992, 39(4): 429-441, or in the article by V. Svyryd et al.: "An analysis of a displacement sensor based on optical fibers", Revista Meixana de Fisica S 52(2): 61-63 (2006)).

Since the reflectance $r_1$ of different surfaces, as can be the case with surfaces of body stones, can vary significantly, a conclusion cannot be made from the reflection signal $I_{\lambda 1}$ about the distance z between the end 18 and the surface 12, even if $d_{\lambda 1}$ (z) is known.

The wavelength λ2 is preferably selected such that the measuring radiation of the wavelength λ2 is more strongly absorbed by the medium 16 than the measuring radiation of the wavelength λ1. In particular, the wavelength λ2 is selected such that the reflection signal $I_{\lambda 2}$ decreases within a desired distance $z_{limit}$ to less than a fraction p of the maximally measurable intensity. λ2 is preferably selected such that the second reflection signal $I_{\lambda 2}$ at a distance from the end of the waveguide below a predetermined maximum distance decreases to a fraction of less than 20%, preferably of less than 10%, further preferably of less than 5%, of the maximally measurable intensity $I_{02}$.

For the wavelength λ2, the equation (1) is expanded by an exponential factor following the Beer-Lambert law:

$$I_{\lambda 2}=I_{02} \cdot r_2 \cdot d_{\lambda 2}(z) \cdot \exp(-2\alpha z) \tag{2}$$

α is the absorption coefficient of the medium 16 in the case of the wavelength λ2. The factor 2 in the exponent emerges from twice passing through the distance z between the end 18 of the waveguide 20 and the surface 12.

In the case of the same illumination and detection geometry for both wavelengths λ1 and λ2, it is $d_{\lambda 1}$ (z)~$d_{\lambda 2}$ (z). If the ratio of the two reflection signals $I_{\lambda 2}:I_{\lambda 1}$ is formed, this ratio thus depends on the distance z according to an exponential course:

$$I_{\lambda 2}:I_{\lambda 1}=(I_{02}:I_{01}) \cdot (r_2:r_1) \cdot \exp(-2\alpha z) \tag{3}$$

If $I_{01}$ and $I_{02}$ are the same or roughly the same for the two wavelengths λ1 and λ2, and the reflectances $r_1$ and $r_2$ are the same or approximately the same for the two wavelengths λ1 and λ2, the equation (3) is reduced to the exponential factor. When the absorption of the medium 16 in the case of the wavelength λ2 is at least approximately known or determinable, the distance z can therefore be precisely determined by solving the equation (3) for z. The above-mentioned assumptions are, however, not applicable in all cases. In practical applications, it is also not required to precisely know the value of the distance z, but rather it may be sufficient to detect whether the distance z is within a distance range below a predetermined maximum distance and/or above a predetermined minimum distance. The measuring method 40 can therefore be carried out such that it is determined whether a predetermined maximum distance is undercut and/or a predetermined minimum distance is exceeded in order to then, if this is the case, generate a trigger signal, for example to trigger a process or an action, such as for example enabling a device. This will be described below.

To verify the equation (3), exemplary measurements have been carried out. FIG. 3a shows a diagram of curves of exemplary measurements, which have been carried out with a measuring device similar to the measuring device 10 in FIG. 1 using electromagnetic measuring radiation of a first wavelength λ1=520 nm and of a second wavelength λ2=1310 nm on a mirror and two human stones as objects 14 in water as medium 16. The absorption coefficient of water at a temperature of 25° C. is $3.035 \times 10^{-5}$ mm$^{-1}$ at 520 nm and 0.7708 mm$^{-1}$ at 1310 nm. The curve 50 shows the distance dependency of the reflection signal $I_{\lambda 1}$ for the mirror, the curve 52 the distance course of the reflection signal $I_{\lambda 1}$ for the first stone and the curve 54 the distance course of the reflection signal $I_{\lambda 1}$ for the second stone. The curve 56 shows the distance course of the reflection signal Ike for the mirror, the curve 58 the distance course of the reflection signal $I_{\lambda 2}$ for the first stone and the curve 60 the distance course of the reflection signal Ike for the second stone. The reflection signals $I_{\lambda 1}$ are standardized in FIG. 3a to $I_{01}$ and the reflection signals $I_{\lambda 2}$ to $I_{02}$. FIG. 3b shows the distance course of the ratio $I_{\lambda 2}:I_{\lambda 1}$ for the mirror (curve 62), the first stone (curve 64) and the second stone (curve 66). $I_{\lambda 1}$ and $I_{\lambda 2}$ are in turn standardized to $I_{01}$ or $I_{02}$. The curves 56, 58 and 60 in FIG. 3a decrease, in comparison to the curves 50, 52, 54, notably more quickly with increasing distance between the end 18 of the waveguide 20 and the surface 12 of the respective target object. The exponential decrease of the ratio $I_{\lambda 2}:I_{\lambda 1}$ described according to equation (3) emerges from the curves 62, 64 and 66 in FIG. 3b). All measuring curves have been standardized to the respective maximum. The extension of the abscissa in FIG. 3b) compared to the abscissa in FIG. 3a) should be noted here.

Generally, the second wavelength λ2 can be selected such that the absorption coefficient of the medium 16 in the case of the wavelength λ2 differs from the absorption coefficient in the case of the wavelength λ1 by a factor of at least 100, preferably of at least 1000, further preferably of at least 10000. In the exemplary measurement, the absorption coefficient of water for λ2 differs from the absorption coefficient for λ1 at a temperature of 25° C. even by a factor of over 25,000.

If, in the equation (3), the reflectances $r_1$, $r_2$ and/or the maximum signal intensity $I_{01}$, $I_{02}$ are not substantially the same and are also not known, it may be appropriate to select the wavelength λ2 such that reflection signals can only be measured from when a predetermined or desired maximum distance $z_{limit}$ is undercut. This can be ensured by a correspondingly high absorption coefficient. For example, in the case of a wavelength λ2=1310 nm, the reflection signal Ike of a mirror in water, depending on the numerical aperture of the waveguide and angle of incidence on the mirror, can decrease within 1 mm to roughly 4% of the maximum value, as emerges from FIG. 4*a*) from a measuring curve 68 for the reflection signal $I_{λ,2}$. FIG. 4*a*) shows by way of example the measured distance course of the reflection signal $I_{λ,1}$ (curve 70) for λ1=520 nm and the distance course of the ratio $I_{λ,2}$:$I_{λ,1}$ (curve 72) for a mirror. Since the intensity of the measuring radiation for the wavelength λ1 at the end 18 of the waveguide 20 was lower by a factor of 10 than in the case of the other measurements, the reflection signals have been multiplied accordingly by 10 for the wavelength λ1. FIG. 4*b*) to e) show further exemplary measurements on different body stone samples in water/buffer solution. The measurement values have only been substrate-corrected, not standardized. In FIG. 4*b*) to e), the measurement scales have been omitted at the ordinate for reasons of clarity. The measurements have, however, resulted in the absolute values of the reflection signals of the different body stones differing by a factor of >5 both for the wavelength λ1=520 nm and for the wavelength λ2=1310 nm and the ratios $I_{λ,2}$:$I_{λ,1}$ substantially following the course of the curves for the wavelength λ2, but being closer to one another in terms of value. It can follow from this that the reflectance $r_1$ for λ1 is sufficiently similar to the reflectance $r_2$ for λ2 for the different body stones to be able to "standardize" the reflection signals for λ2 with the reflection signals for λ1.

Figure 5:
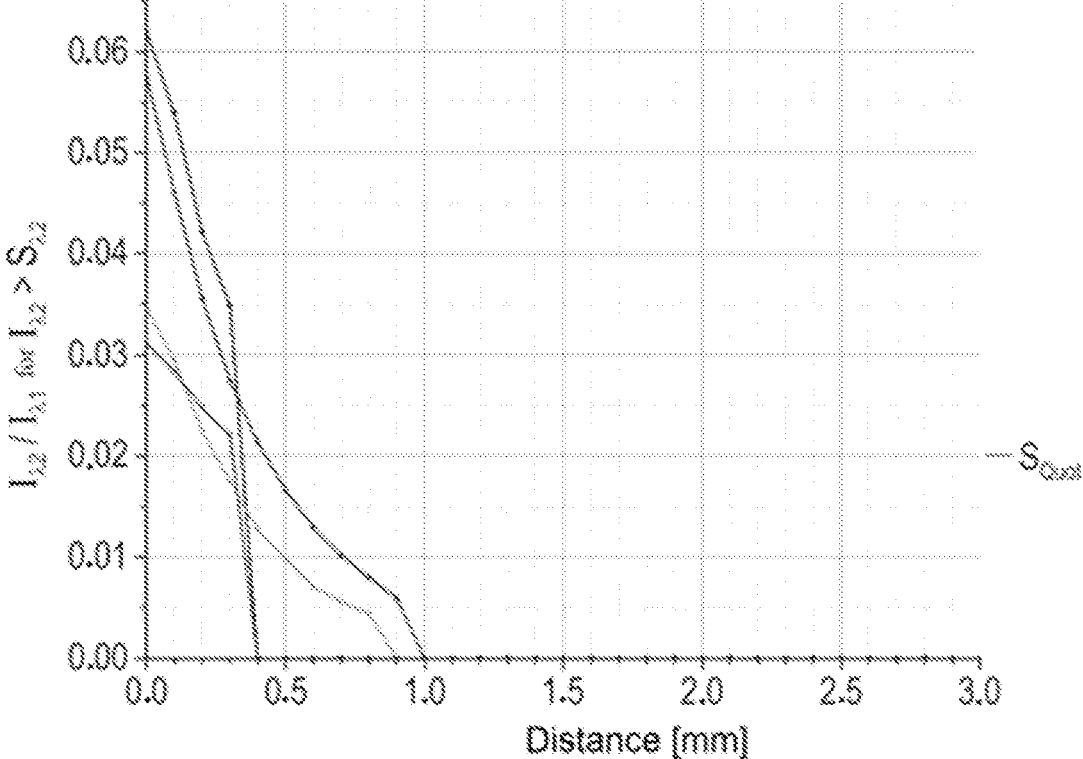
FIG. 5 is a further diagram showing the ratios of reflection signals of surfaces of different target objects for two different wavelengths in a practical implementation of the measuring method.

If the distance measurement is carried out for the purpose of detecting whether the end 18 of the waveguide is located at a distance to the surface 12 of the target object, which is shorter than or at best the same as a predetermined maximum distance $z_{limit}$, it is advantageous for the practical implementation of the measuring method according to the invention when a threshold value $S_{λ,2}$ is predetermined for the reflection signal $I_{λ,2}$ as a function of the predetermined maximum distance $z_{limit}$. Furthermore, it is advantageous to also predetermine a threshold value $S_{quot}$ for the ratio $I_{λ,2}$:$I_{λ,1}$ as a function of $z_{limit}$. In FIG. 5, the distance course of the ratio $I_{λ,2}$:$I_{λ,1}$ is shown for $I_{λ,2}$>$S_{λ,2}$ from the curves in FIG. 4*d*) to e). The threshold value $S_{λ,2}$ used for FIG. 5 has been set at 0.0025 V and the curves for the ratio $I_{λ,2}$:$I_{λ,1}$ taken from FIG. 4*b*) to e) have been multiplied by a step function which is 1 for $I_{λ,2}$>$S_{λ,2}$ and otherwise is 0. The threshold value $S_{quot}$ can for example be set to 0.02. When the measuring method is used in this manner for laser lithotripsy, this means, according to FIG. 5, that body stones are treated with lithotripsy only at a distance of <0.5 mm between the end 18 of the waveguide 20 and the surface 12 of the respective body stones.

As emerges from the above description, it is advantageous when the measured reflection signal $I_{λ,2}$ strongly decreases as a function of the distance. A change in the distance behavior of the reflection signal can be achieved, instead of using long-wave measuring radiation, in which the medium 16 has a high absorption, also by using different ways of coupling the measuring radiation into the waveguide 20, in particular by utilizing the numerical aperture of the waveguide 20 in different manners and/or by coupling obliquely in relation to the longitudinal axis of the waveguide, with which donut modes can be generated.

If the measuring radiation is coupled into the waveguide 20 at an opening angle (aperture) that is smaller than the angle of acceptance of the waveguide, the opening angle (aperture) of the exiting light beam is generally also smaller and the reflection signal decreases more slowly with increasing distance. If, conversely, the measuring radiation is coupled into the waveguide 20 at a greater opening angle, for example the same as the angle of acceptance of the waveguide 20, the opening angle of the exiting light beam is generally also greater and the reflection signal decreases more quickly with increasing distance. In the case of coupling in the measuring radiation 26 obliquely to the waveguide axis, a donut-shaped beam profile is created, whose reflection signal decreases even more quickly. This possibility of adjusting the coupling may be helpful if the measuring light source 22 in FIG. 1 cannot provide a measuring radiation with a wavelength that is absorbed by the medium 16 to the desired extent. In principle, the wavelengths λ1 and λ2 in the case of this embodiment of the measuring method can be the same or virtually the same, wherein the respective measuring radiation generated by the light sources $L_{λ,1}$ and $L_{λ,2}$ is coupled into the waveguide 20 simply in a different manner (opening angle and/or orientation).

Figure 6:
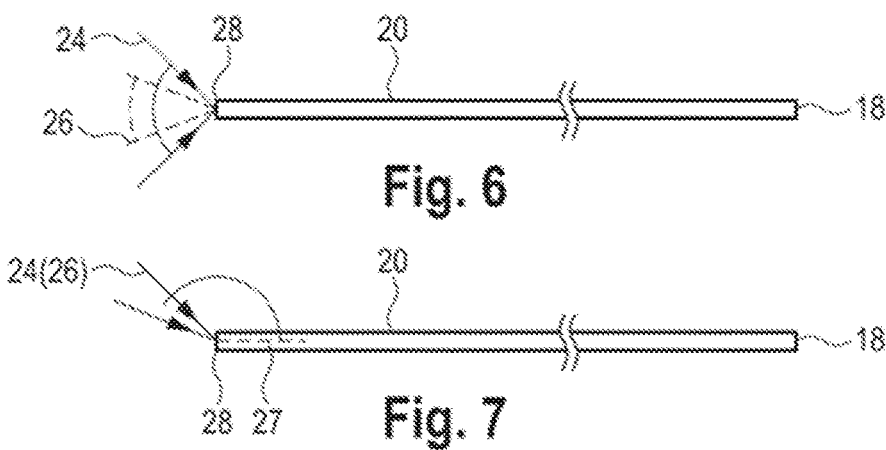
FIG. 6 is a schematic diagram of different couplings of measuring radiation in an optical waveguide.
Figure 7:
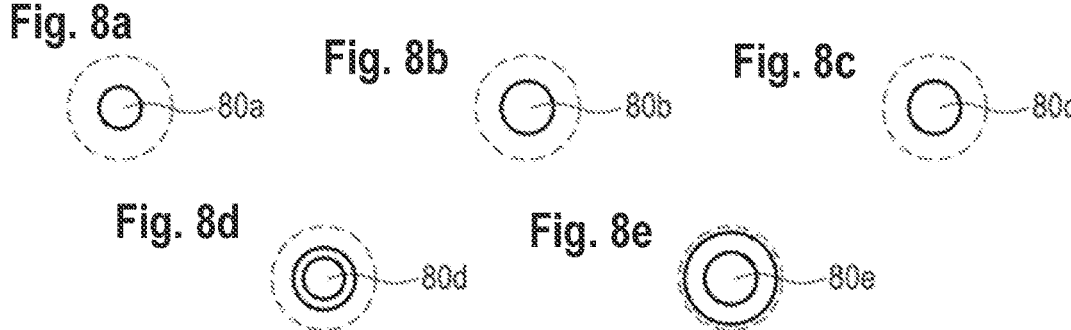
FIG. 7 is a further schematic diagram of the coupling of measuring radiation into an optical waveguide.

FIG. 6 shows the coupling of measuring radiation 24 at a large opening angle and the coupling of the measuring radiation 26 at a smaller opening angle and FIG. 7 shows the coupling of measuring radiation 24 into the waveguide 28 obliquely to the waveguide axis 27 of the waveguide 20, while the measuring radiation 26 (not shown) is for example coupled collinearly to the waveguide axis 27.

FIG. 8*a*) to e) show different beam profiles of measuring radiation at a distance of 50 mm from the end 18 of the waveguide 20. FIG. 8*a*) shows a beam profile 80*a* with a small aperture, FIG. 8*b*) a beam profile 80*b* with a medium aperture, and FIG. 8*c*) a beam profile 80*c* with a maximum aperture. FIG. 8*d*) shows a beam profile 80*b* in the form of a donut profile with a small aperture and FIG. 8*e*) a beam profile 80*e* in the form of a donut profile with a large aperture. The uninterrupted circle lines illustrate the maximally usable aperture of the waveguide 20.

Figure 9:
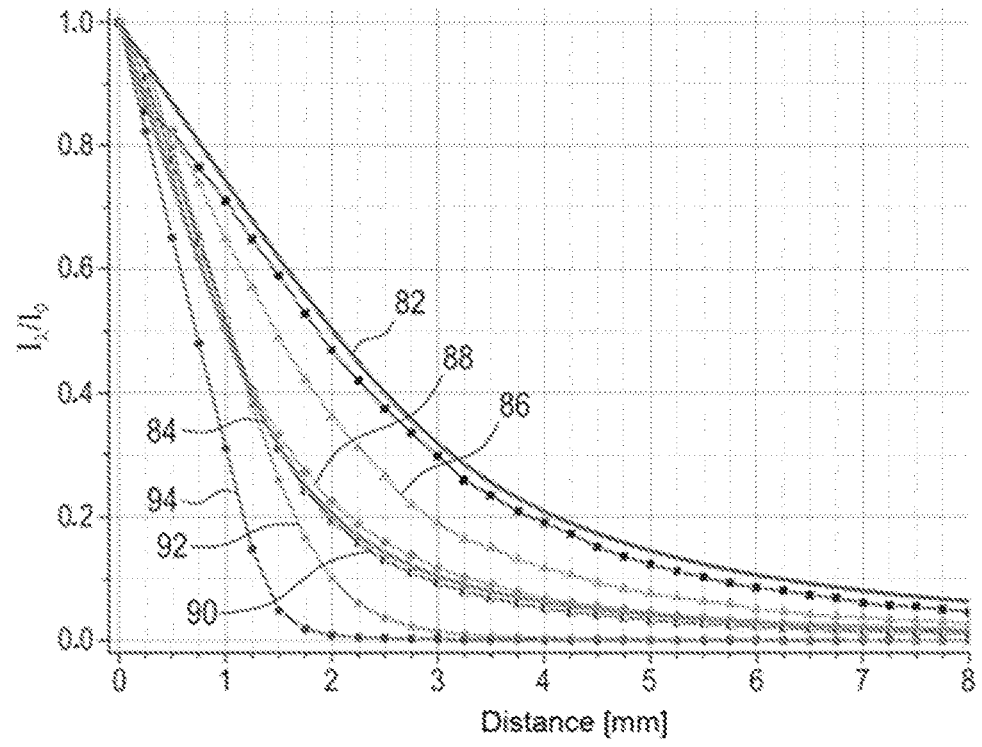
FIG. 9 is a diagram of reflection signals for the different radiation profiles in FIG. 8a) to e) as a function of the distance of the end of the waveguide from a surface of a target object.

FIG. 9 shows the distance behavior of a reflection signal $I_λ$ for different ways of coupling measuring radiation into the waveguide 20. The wavelength observed here is 520 nm, the medium is water. The two curves without symbols in FIG. 9 show the calculated distance behavior of the reflection signal $I_λ$ for a waveguide in the form of a fiber with a core diameter of 365 μm and a numerical aperture 0.11 (curve 82) and a numerical aperture of 0.22 (curve 84). It can be shown from this that the selection of a waveguide with a higher numerical aperture leads to a quicker decrease of the reflection signal $I_λ$ with increasing distance. The curves with symbols in FIG. 9 show measurements on a mirror in water, in which the numerical aperture of the waveguide 20 has been utilized differently or the measuring radiation has been coupled into the waveguide 20 in a skewed manner. The curve 86 shows the distance behavior of the reflection signal $I_λ$ for coupling the measuring radiation into the waveguide 20, which generates the beam profile according to FIG. 8*a*). The curve 88 shows the distance behavior of the reflection signal $I_\lambda$ for coupling, which generates the beam profile 80*b* according to FIG. 8*b*). The curve 90 shows the distance behavior of the reflection signal $I_\lambda$ for coupling the measuring radiation, which generates the beam profile 80*c* according to FIG. 8*c*). The curve 92 shows the distance behavior of the reflection signal $I_\lambda$ for coupling, which generates the beam profile 80*d* according to FIG. 8*d*). The curve 94 shows the distance behavior of the reflection signal $I_\lambda$ for coupling, which generates the beam profile 80*e* according to FIG. 8*e*). It follows that the reflection signal as a function of the distance decreases increasingly more quickly with increasing utilization (or filling) of the aperture of the waveguide, and that oblique coupling, which generates a donut beam profile, causes an even quicker decrease of the reflection signal as a function of the distance.

Figure 10:
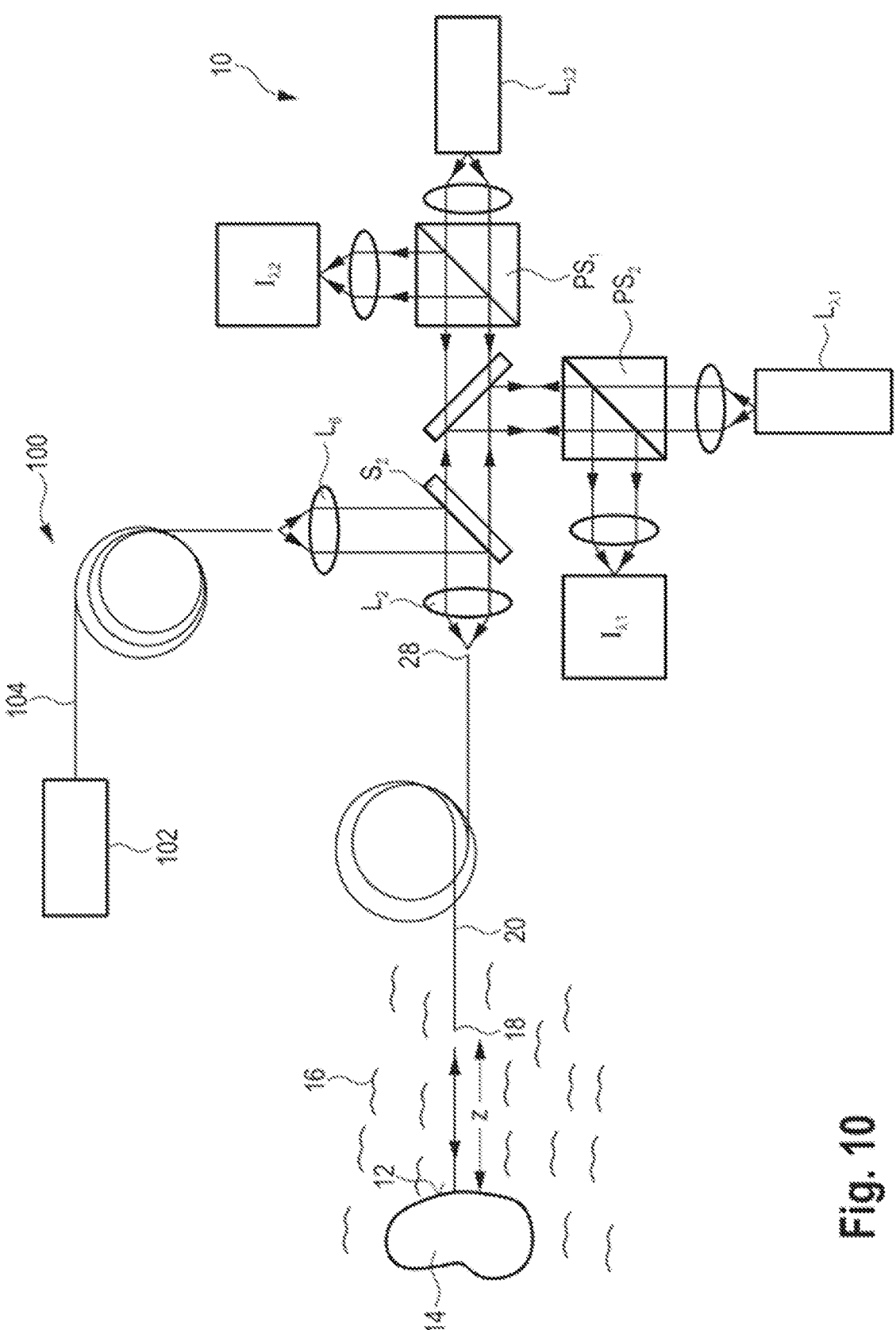
FIG. 10 is a schematic design of a laser lithotripsy device with the measuring device in FIG. 1.

FIG. 10 shows a block diagram of a laser lithotripsy device 100, which can have the measuring device 10 according to FIG. 1 as a component. In addition to the measuring device 10, the laser lithotripsy device 100 has a treatment laser 102, which generates the treatment laser light for breaking up body stones. The treatment laser 102 can be a Holmium laser. The treatment laser light can be coupled into the waveguide 20, which is also used for the measuring radiation, via a waveguide 104, a further lens $L_6$ and a further dichroic mirror $S_2$ and via the lens $L_2$ such that the treatment laser light can exit the end 18 of the waveguide 20. The treatment laser 102 can be enabled by a trigger signal of the evaluation unit 36 (FIG. 1, omitted in FIG. 10 for clarity), when the measuring device 10 detects a distance z of the end 18 of the waveguide 20 from the surface 12 of the target object 14 that is shorter than the maximum distance $z_{limit}$. The maximum distance $z_{limit}$ can be shorter than 1 mm, for example shorter than 0.5 mm. After being enabled, the treatment laser can be activated to emit treatment light. In the case of the lithotripsy device 100, it is therefore ensured that the treatment laser light is only emitted when a body stone is located at a distance in front of the end 18 of the waveguide 20 that is shorter than the maximum distance $z_{limit}$. It may also be advantageous to generate the trigger signal only when the measured distance of the end of the waveguide 20 from the surface 12 of the target object 14 is greater than a minimum distance that is shorter than the maximum distance $z_{limit}$. Additionally, the laser lithotripsy device 100 can have a controller for the treatment laser 102 designed to adjust the pulse energy of the treatment laser light as a function of the measured distance z. For example, the control device can increase the pulse energy if the end 18 of the waveguide 20 is located at a greater distance from the surface of a body stone to be treated, or reduces the pulse energy in the case of a shorter distance. The controller can be integrated into the treatment laser or into the measuring device 10, for example into the evaluation device 36, as hardware or software.

The invention claimed is:

1. A measuring method for optically determining a distance (z) of a surface of a body stone located in a medium from an end of an optical waveguide, comprising:
    emitting electromagnetic measuring radiation of a first wavelength ($\lambda$1) and of a second wavelength ($\lambda$2) from the end of the waveguide towards the surface, wherein the medium more strongly absorbs the electromagnetic measuring radiation of the second wavelength ($\lambda$2) than the electromagnetic measuring radiation of the first wavelength ($\lambda$1), wherein the measuring radiation of the first wavelength ($\lambda$1) is coupled into the waveguide at a first opening angle, which differs from an opening angle at which the measuring radiation of the second wavelength ($\lambda$2) is coupled into the waveguide;
    measuring a first reflection signal ($I_1$) of the electromagnetic measuring radiation of the first wavelength ($\lambda$1) reflected from the surface, and measuring a second reflection signal ($I_2$) of the electromagnetic measuring radiation of the second wavelength ($\lambda$2) reflected from the surface, and
    determining the distance (z) from a ratio ($I_2:I_1$) of the second and the first reflection signal.

2. The measuring method according to claim 1, wherein the determination of the distance (z) comprises determining whether a predetermined maximum distance ($z_{limit}$) is undercut and/or a predetermined minimum distance is exceeded.

3. The measuring method according to claim 2, wherein a trigger signal is generated when the measurement results in the predetermined maximum distance ($z_{limit}$) being undercut and/or the predetermined minimum distance being exceeded.

4. The measuring method according to claim 2, wherein the second wavelength ($\lambda$2) is selected such that the second reflection signal (I2) at a distance from the end of the waveguide below the predetermined maximum distance ($z_{limit}$) decreases to a fraction of less than 20%, preferably of less than 10%, further preferably of less than 5%, of the maximally measurable intensity $I_{02}$.

5. The measuring method according to claim 2, wherein, as a function of the predetermined maximum distance ($z_{limit}$), a first threshold value ($S_{\lambda 2}$) is predetermined for the second reflection signal ($I_2$) and wherein the ratio ($I_2:I_1$) of the second reflection signal and the first reflection signal is multiplied by 1 when the second reflection signal ($I_2$) exceeds the threshold value ($S_{\lambda 2}$) for the second reflection signal ($I_2$) and otherwise is set to zero and wherein, as a function of the predetermined maximum distance ($z_{limit}$), a second threshold value ($S_{quot}$) is predetermined for the ratio ($I_2:I_1$) of the second reflection signal and the first reflection signal.

6. The measuring method according to claim 5, wherein the trigger signal is generated when the ratio ($I_2:I_1$) of the second reflection signal and the first reflection signal exceeds the second threshold value ($S_{quot}$).

7. The measuring method according to claim 1, wherein the second wavelength ($\lambda$2) is selected such that the absorption coefficient ($\alpha$) of the medium in the case of the second wavelength ($\lambda$2) differs from the absorption coefficient in the case of the first wavelength ($\lambda$1) by a factor of at least 100, preferably of at least 1000, further preferably of at least 10000.

8. The measuring method according to claim 1, wherein the first wavelength ($\lambda$1) is in the visible spectral range.

9. The measuring method according to claim 1, wherein the second wavelength ($\lambda$2) is in the near-infrared spectral range.

10. The measuring method according to claim 1, wherein the measuring radiation of the first wavelength ($\lambda$1) or the measuring radiation of the second wavelength ($\lambda$2) is coupled into the waveguide obliquely to the waveguide axis.

11. A measuring device configured to optically determine a distance (z) of a surface of a body stone located in a medium from an end of an optical waveguide comprising:
    a measuring radiation source to generate electromagnetic measuring radiation of a first wavelength ($\lambda$1) and of a second wavelength ($\lambda$2), wherein the medium more strongly absorbs the electromagnetic measuring radiation of the second wavelength ($\lambda$2) than the electromagnetic measuring radiation of the first wavelength ($\lambda$1), wherein the measuring radiation of the first wavelength ($\lambda$1) is coupled into the waveguide at a first opening angle, which differs from an opening angle at which the measuring radiation of the second wavelength ($\lambda$2) is coupled into the waveguide the optical waveguide to emit the electromagnetic measuring radiation from the end of the waveguide towards the surface;

a detection device to measure a first reflection signal ($I_1$) of the electromagnetic measuring radiation of the first wavelength ($\lambda$1) reflected from the surface, and for measuring a second reflection signal ($I_2$) of the electromagnetic measuring radiation of the second wavelength ($\lambda$2) reflected from the surface, and an evaluation unit to determine the distance (z) from a ratio ($I_2$:$I_1$) of the second and the first reflection signal.

12. The measuring device according to claim 11, wherein the measuring radiation source has a first laser ($L_{\lambda 1}$) for generating the electromagnetic measuring radiation of the first wavelength ($\lambda$1) and a second laser ($L_{\lambda 2}$) for generating the electromagnetic measuring radiation of the second wavelength ($\lambda$2).

13. The measuring device according to claim 11, wherein the optical waveguide has a numerical aperture of greater than 0.1, preferably greater than 0.2.

14. A laser lithotripsy device for breaking up body stones, with a treatment laser for emitting treatment laser light and a measuring device according to claim 11.

15. The laser lithotripsy device according to claim 14, wherein the evaluation unit of the measuring device generates a trigger signal for enabling the treatment laser when a distance (z) of the end of the waveguide is measured from the surface of a body stone to be broken up that is shorter than a predetermined maximum distance ($z_{limit}$).

16. The laser lithotripsy device according to claim 15, wherein the trigger signal is generated when the measured distance (z) of the end of the waveguide from the surface is greater than a minimum distance that is shorter than the maximum distance.

17. The laser lithotripsy device according to claim 14, wherein a control device for the treatment laser adjusts the pulse energy of the treatment laser light as a function of the measured distance (z).

\* \* \* \* \*